United States Patent [19]
Clarke et al.

[11] Patent Number: 5,149,336
[45] Date of Patent: Sep. 22, 1992

[54] DISPOSAL BREAST PADS FOR NURSING MOTHERS

[76] Inventors: Haley C. Clarke, 4798 Deer Run, NE., Kennesaw, Ga. 30114; Lisa C. Panoz, Rte. 1, Box 12828, Hwy. 211, Hoschton, Ga. 30548

[21] Appl. No.: 679,772

[22] Filed: Apr. 3, 1991

[51] Int. Cl.⁵ ..................... A61F 13/15; A61F 13/20
[52] U.S. Cl. .................... 604/388; 604/385.1; 604/358
[58] Field of Search ............ 604/358, 378, 385.1, 604/386, 387, 388

[56] References Cited

U.S. PATENT DOCUMENTS

| | | | |
|---|---|---|---|
| D. 246,729 | 12/1977 | Murphy | D24/99 |
| 2,436,977 | 3/1948 | Stevens | 2/42 |
| 2,492,303 | 12/1947 | Lo Cascio | 2/42 |
| 2,630,119 | 3/1953 | Aagesen | 128/280 |
| 2,748,771 | 6/1956 | Richards | 128/280 |
| 2,767,402 | 10/1956 | Pauk | 604/385.1 X |
| 2,896,623 | 7/1959 | Fitzgerald | 604/385.1 |
| 3,356,090 | 12/1967 | Plantinga et al. | 604/385.1 X |
| 3,502,083 | 3/1970 | Howard et al. | 604/385.1 X |
| 3,738,362 | 6/1973 | Sneider | 604/385.1 X |
| 4,047,534 | 9/1977 | Thomaschefsky et al. | |
| 4,074,721 | 2/1978 | Smits et al. | |
| 4,125,114 | 11/1978 | Repke | 604/385.1 X |
| 4,164,228 | 8/1979 | Weber-Unger | 604/385.1 |
| 4,193,404 | 3/1980 | Repke et al. | 604/385.1 X |
| 4,875,492 | 10/1989 | Mitchell et al. | 604/378 X |
| 4,892,532 | 1/1990 | Boman | |
| 4,908,026 | 3/1990 | Sukiennik et al. | 604/378 |
| 4,923,454 | 3/1990 | Seymour et al. | |
| 4,935,022 | 6/1990 | Lash et al. | 604/368 |

Primary Examiner—David Isabella
Assistant Examiner—Elizabeth M. Burke
Attorney, Agent, or Firm—Hurt, Richardson, Garner, Todd & Cadenhead

[57] ABSTRACT

A disposable, contoured, form fitting, absorbent breast pad comprising three layers, an inner fluid wicking layer, a central fluid absorbent layer, and an outer moisture resistant layer, which is generally tear drop in shape and dome-like in cross-section and is large enough to encompass substantially the entire female breast and to fill substantially the average nursing and maternity bra cup.

15 Claims, 5 Drawing Sheets

DISPOSAL BREAST PADS FOR NURSING MOTHERS

BACKGROUND OF THE INVENTION

1. Field of the Invention

The present invention relates generally to a means for preventing breast milk leakage from the breasts of nursing women from seeping into and through clothing. The invention relates specifically to disposable, contoured, absorbent breast pads which fit within the brassiere cup to absorb any breast milk leakage from the breasts of nursing women and preventing such breast milk from contacting and seeping into and through clothing.

2. Description of the Prior Art

Devices for preventing breast milk leakage from contacting and seeping into and through clothing currently are available on the market. Generally, these devices fall into two broad categories, nursing or breast pads and nursing or protective brassieres. These two broad categories each comprise two general sub-categories, reusable pads and disposable pads, and unitary brassieres and brassieres having replaceable absorbent pads. Each of the devices currently comprising the above categories suffers from at least one disadvantage, including low moisture absorbency, visibility of the device through clothing, bulkiness, inability to keep the moisture of the breast milk away from both the skin and clothing, poor fit within the brassiere, lack of multiple sizes for accommodating the different size breasts from one women to the next, lack of separately shaped pads for the left breast and the right breast, and designs ignoring the proper anatomical shape of the female breast.

The U.S. Patent to Mitchell et al., U.S. Pat. No 4,875,492, discloses a washable and contoured nursing pad. The nursing pad is molded into a contoured shape and consists of multiple layers including a slip resistant outer layer, a waterproof second layer, a fluid absorbent third layer, and an inner layer. The disadvantages associated with the Mitchell pad include its contoured shape which, instead of molding to the shape of the wearer's breast, molds the wearer's breast to the shape of the pad, resulting in discomfort. Additionally, the Mitchell pad is somewhat smaller than the actual breast, covering only the nipple portion and surrounding area, and thus is susceptible to movement within the brassiere and around the breast. An additional disadvantage of the Mitchell pad is the bonding of the multiple layers around its outer edges, which may allow leakage of fluid from or around these edges and into the wearer's clothing. One last disadvantage is the "one size fits all" nature of the Mitchell pad which may result in unnecessary movement of the pad, incomplete coverage of the breast, and visibility through the wearer's clothing.

The U.S. Patent to Weber-Unger, U.S. Pat. No. 4,164,228, discloses an absorbent pad for nursing brassieres with a capped shaped to fit around the breast and a lower apron to increase the absorption volume of the pad below the breast. The disadvantages associated with the Weber-Unger pad include its generally hemispherical shape which is both uncomfortable to the wearer and will not reduce movement when placed within the brassiere cup. The lower depending apron portion presents two distinct disadvantages. First, it creates a shape which is not complimentary to the shape of the brassiere cup and, therefore, will not easily fit within the brassiere cup. Secondly, fluid which may accumulate in this apron may leak around its edges and seep into the brassiere or, indeed, into the garment below the brassiere.

The U.S. patent to Smits et al., U.S. Pat. No. 4,074,721, discloses a generally hemispherical device having a moisture permeable outer portion, an absorbent central portion, and fluid-transmitting body-contacting inner portion. The generally hemispherical shape of this device does not complement the natural shape of the female breast and may create discomfort when used. Additionally, the shape of the device is not complimentary to the typical brassiere and may be susceptible both to movement within the brassiere due to this difference and to visibility thorough the brassiere and the outer garments. The Smits pad also has the disadvantage of having a typical edge seal which may allow the leakage of fluid around the edge seal and into the wearer's clothing.

The U.S. patent to Thomaschefsky et al., U.S. Pat. No. 4,047,534, discloses a nursing pad comprising a three-layer structure having an outer layer web of synthetic thermoplastic polymeric microfibers, a middle absorbent layer and an inner layer composed of a lightweight thermoplastic synthetic web. The disadvantages attributable to the Thomaschefsky device include a generally circular, flat configuration which is not complimentary to the typical brassiere and may have a tendency both to move within the brassiere and to deform the brassiere, thus showing through the wearer's clothing. This configuration also is not complimentary to the natural shape of the female breast and may produce discomfort to the wearer. A further disadvantage is that the inner and outer layers, being bonded together at the periphery of the pad, may allow fluid which is gathered at the lower edge of the pad to leak around the bond and to contact and to seep into or through the wearer's clothing.

The U.S. Patent to Plantinga et al., U.S. Pat. No. 3,356,090, discloses a three zone device, comprising an inner zone of a synthetic cellular material which allows fluid to move through to the second zone which comprises several layers of fluid absorbent material. The outer third zone is a fluid repellant material to prevent seepage through to the wearer's garment. The disadvantages attributable to the Plantina patent include its generally circular shape and semispherical cross-section. The generally circular shape may not conform to the typical brassiere and the device may not be held securely within the brassiere, thus causing discomfort and, possibly, moving to such a position that it will not absorb fluid. The generally semispherical cross-section may not conform to the natural shape of the female breast and may cause discomfort to the wearer. Additionally, the various zones are bonded together along the periphery of the pad, thus possibly allowing fluid to seep around the water repellant outer layer and contact or seep into or through the wearer's garments.

The U.S. patent to Aagesen, U.S. Pat. No. 2,630,199, comprises a dual layer pad having an inner layer of an absorbent material and an outer layer of a water resistant material. The entire pad is surrounded by a gauze so as to hold the pad in an assembled relation. The disadvantages attributable to the Aagesen device include the likelihood of leakage from the pad around its periphery, allowing any fluid gathered to contact the wearer's garments. A further disadvantage is the nature of the absorbent material of the device which may not contain fluid for an extended period of time. An additional disadvantage is the device's generally circular shape which does not compliment the typical brassiere cup.

The U.S. patent to Murphy, U.S. Pat. No. 246,729, discloses an ornamental design for a combined breast shield and milk collector. This generally circular device has a semispherical cross-section and suffers from the same disadvantages as the generally circular devices with semispherical cross-sections discussed above.

The U.S. patents to Richards. U.S. Pat. No. 2,748,771, Lo Cascio, U.S. Pat. No. 2,429,303 and Stevens. U.S. Pat. No. 2,436,977, disclose devices which incorporate entire brassiere-like components. The Richards device combines a brassiere and a replaceable absorbent pad of any design. The Lo Cascio device discloses a brassiere having breast pockets which may be opened to expose the breast for nursing. The Stevens device is basically a waterproof shield to be worn between the body and the brassiere.

The U.S. patents to Seymour et al., U.S. Pat. No. 4,923,454, Bowman. U.S. Pat. No. 4,892,532, and Lash et al., U.S. Pat. No. 4,935,022, disclose various absorbent or absorbing articles. The Seymour et al. device discloses absorbent articles comprising hydrophilic polymeric components. The Bowman device discloses absorbent articles comprising a liquid-permeable casing consisting of a thin, spun-bonded hydrophobic fibrous fabric fabric layer adapted to face the user. The Lash et al. device discloses absorbent articles comprising a hydrogel-forming polymeric gelling agent.

SUMMARY OF THE INVENTION

The present invention is a disposable, contoured, form fitting, absorbent breast pad. Each pad is generally tear drop in shape and large enough to fill the average nursing and maternity brassiere cup. As the pad is contoured to fit the natural shape of the typical female breast, a left pad and a right pad are necessary which generally are mirror images of each other. Additionally, the pads are provided in various sizes, generally small, medium, and large, to fit various sized women. The pads are contoured in a dome-like fashion to encompass the entire breast.

The pad is structured as three-layer device. The inner layer, which contacts the breasts, is a soft, moisture drawing fabric which wicks the leaking breast milk fluid away from the breast and into the central absorbent layer. The inner layer is made from a material that remains as dry as possible after wicking the fluid through to reduce moisture-related irritation and discomfort to the wearer's skin. The central absorbent layer absorbs and retains the fluid after it has passed through the inner layer. Although any conventional absorbent material is suitable, the use of an absorbent material containing or impregnated with a moisture gelling agent is preferred to help prevent fluid leakage. The outer layer is a moisture-resistant, noncrinkly material which covers at least the entire outside of the pad and prevents the absorbed fluid from contacting the wearer's brassiere and other garments.

The thickness of the central absorbent padding is graduated, being thinnest at the top of the pad, gradually thickening until it is thickest around the nipple area, and then gradually thinning toward the bottom and outside edges of the pad. The moisture-resistant outer layer also wraps around the bottom edge of the pad and extends upwardly along the inner side of the pad, thus wrapping around the bottom edge of the central absorbent layer and the inner wicking layer, creating a cuplike lower barrier or well and inner dam. As fluid has a tendency to gravitate to the lowermost edge of a pad, this moisture-resistant material sided well further prevents fluid absorbed in the central absorbing layer from leaking out the bottom of the pad or around the lower edge of the pad where the three layers are bonded together.

Accordingly, it is an object of the present invention to provide a disposable breast pad for nursing mothers which will prevent the leakage of breast milk into and through the wearer's garments.

It is another object of the present invention to provide a breast pad which comprises a variable thickness absorbent layer placing more absorbent pad in areas where such absorbency is needed.

It is a further object of the present invention to provide a breast pad which has an inner contour complimenting the natural shape of the female breast so as to provide more comfort for the wearer.

It is still another object of the present invention to provide a breast pad which has an outer contour complimentary to the typical brassiere, thus preventing movement or slippage of the pad within the brassiere and to decrease or eliminate visibility of the pad through the wearer's garments.

Yet another object of the present invention is to provide a breast pad which has a moisture-resistant outer layer extending over the entire outer surface of the pad and further extending a certain distance around the bottom edge of the pad and upwardly along the inner side of the pad to provide a lower barrier or well and inner dam to contain any fluid gathering within the bottom edge of the pad.

Still another object of the present invention is to provide a breast pad which comes in various sizes for different sized women.

It is an object of the present invention to provide a set of breast pads which are individually contoured for the left breast and the right breast for increased comfort to the wearer.

A still further object of the present invention is to provide a breast pad which uses current thin absorbent pad technology so as to reduce the bulkiness of the pad such that the pad will be less visible or invisible through the wearer's garments.

It is a still further object of the present invention to provide a breast pad which includes a noncrinkling, moisture-resistant outer layer thus eliminating the noise made from the typical plastic moisture-resistant layer used on many currently available breast pads.

Another object of the present invention is to provide a breast pad which is of such a size that it will encompass the entire breast, resulting in greater absorbency, less of a tendency to move when used properly, and a lower likelihood of showing through the wearer's garments.

It is still another object of the present invention to provide a breast pad which is composed of materials which are nonirritating to the breast skin and will not cause the generally tender nursing breast further discomfort.

Another object of the present invention is to provide a breast pad which is economical to manufacture and simple to use.

These objects and other objects, features and advantages will become apparent to one skilled in the art when the following Detailed Description of a Preferred Embodiment is read in conjunction with the accompanying drawings in which like reference numerals correspond to like components throughout the several views.

BRIEF DESCRIPTION OF THE DRAWINGS

FIG. 1 is a front elevation of the breast pads of the present invention with FIG. 1a being the right breast pad and FIG. 1b being the left breast pad.

FIG. 2 is a rear elevation of the breast pads of the present invention with FIG. 2a being the left breast pad and FIG. 2b being the right breast pad.

FIG. 3 is a cross-sectional view of the breast pads of the present invention with FIG. 3a being taken along line 3a—3a of FIG. 1a and FIG. 3b being taken along line 3b—3b of FIG. 1b.

FIG. 4 is a cross-sectional view of the breast pads of the present invention with FIG. 4a being taken along line 4a—4a of FIG. 1a and FIG. 4b being taken along line 4b—4b of FIG. 1b.

DETAILED DESCRIPTION OF A PREFERRED EMBODIMENT

Figure 1A:
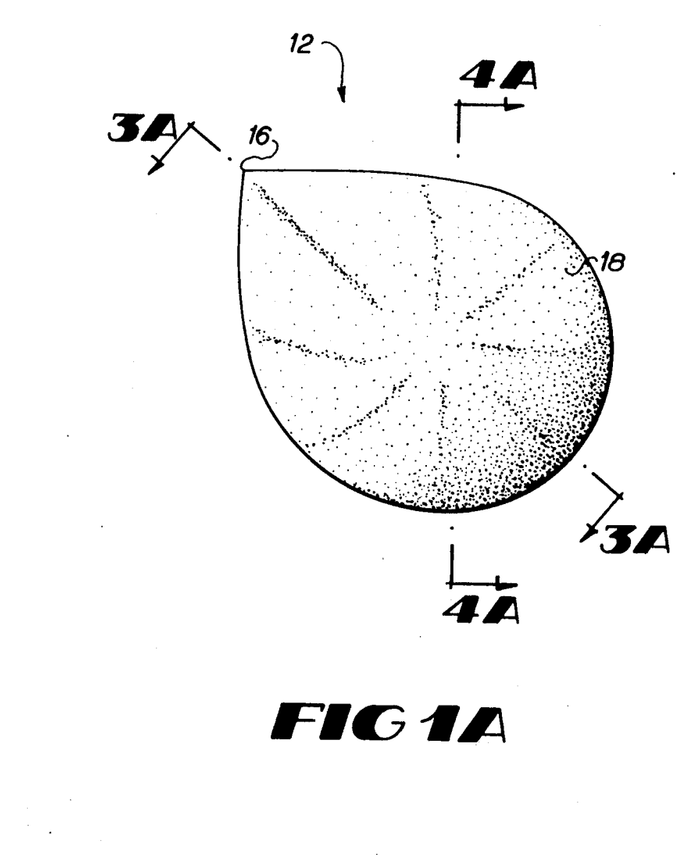
Figure 1B:
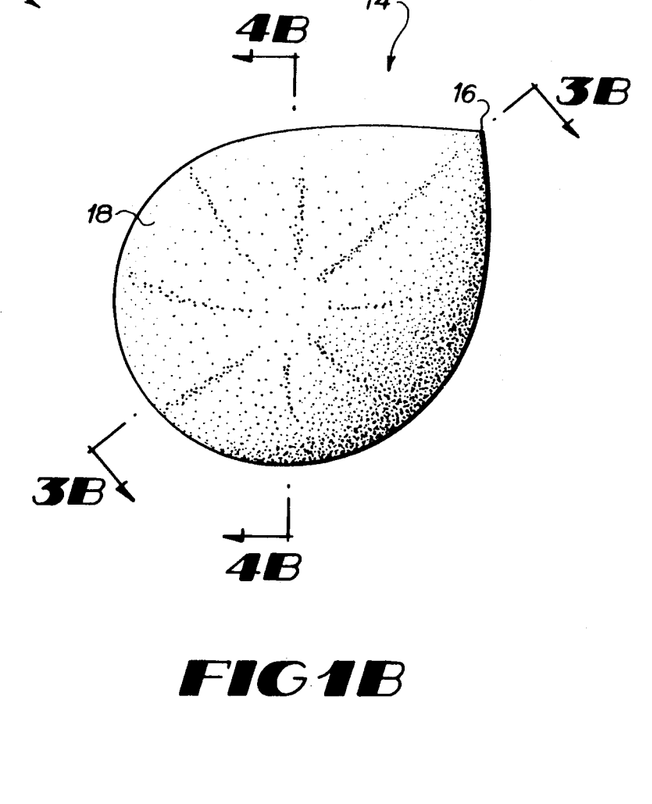
Figure 2A:
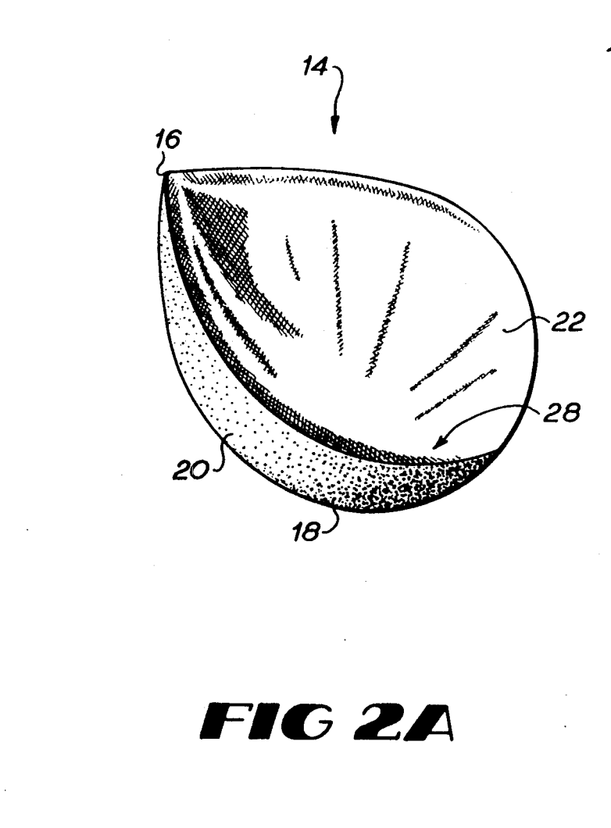
Figure 2B:
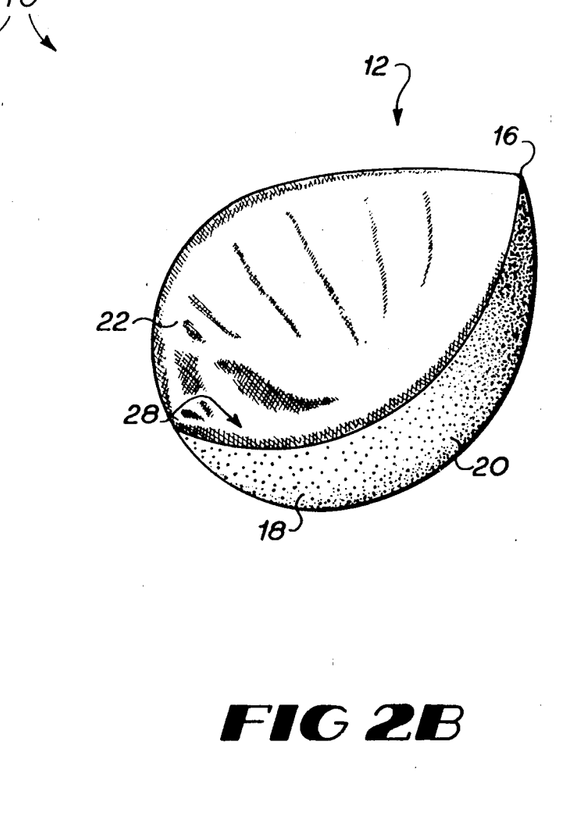
Figure 5:
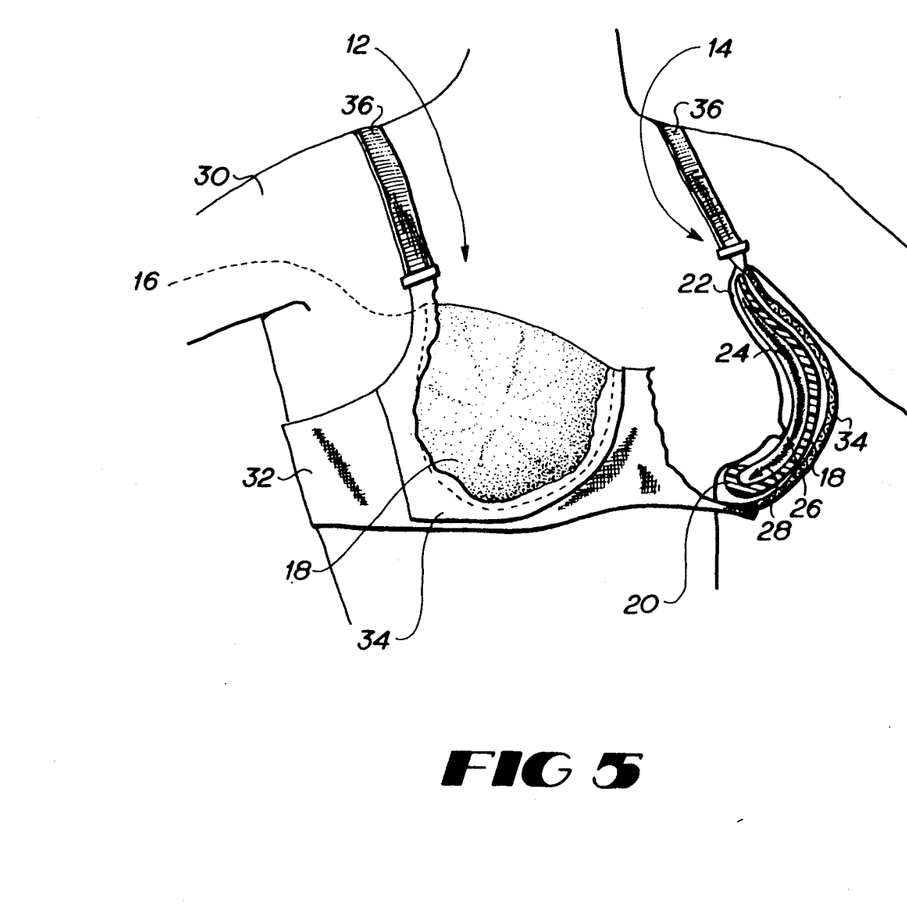
FIG. 5 is a front perspective view of the breast pads of the present invention contained within a brassiere on a wearer, a portion of the brassiere being broken away to show the positioning of the right breast pad within the brassiere, and a portion of the brassiere being shown in the cross-section to show a cross-section of the left breast pad of the present invention.

Referring now to FIGS. 1, 2 and 5, the preferred embodiment of the breast pads 10 for nursing mothers are supplied in pairs, a right pad 12 contoured to encompass the typical right breast and a left pad 14 contoured to encompass the typical left breast. The pads 10 have a generally tear drop shape having an upper tear drop point 16 corresponding to the upper point in brassiere 32 where the brassiere cup 34 attaches to the brassiere strap 36. The lower, rounded portion of the tear drop shape corresponds to the generally rounded lower edge of the brassiere cup 34.

Figure 3A:
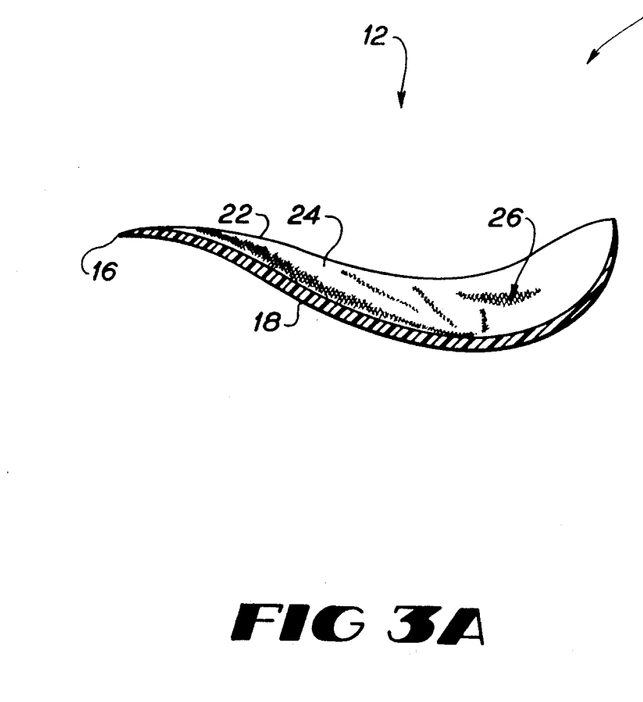
Figure 3B:
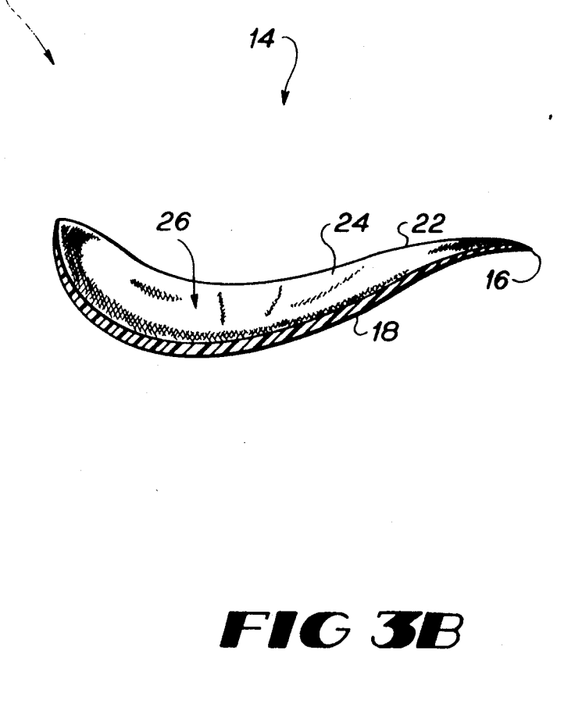
Figure 4A:
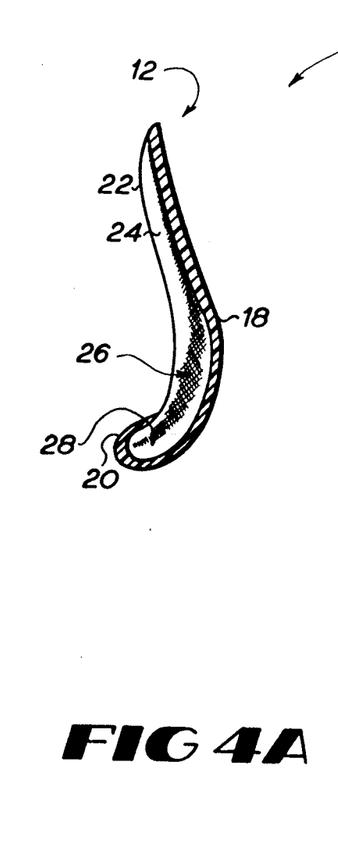
Figure 4B:
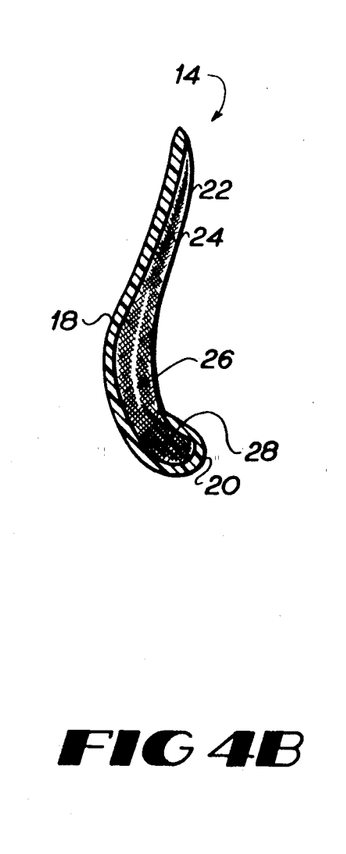

Referring now to FIGS. 3 and 4, the breast pads 10 are comprised of three layers of different types of material for different purposes. The inner wicking layer 22 is generally a soft, comfortable cotton mesh or a similar type material which allows fluid to be wicked through this material into the central absorbent layer 24. The purpose of the inner wicking layer 22 is to have a comfortable texture and to be a protective barrier against wetness from the fluid from contacting the skin to help prevent irritation of the wearer's skin. The inner wicking layer 22 should be of such a material that it will remain as dry as possible once the fluid has wicked through to the central absorbent layer 24. A suitable inner wicking layer 22 material also is a thin hydrophobic material which is liquid permeable and thus allows fluid to wick through it to the central absorbent layer 24, while itself remaining dry and comfortable to the wearer. Such a material is disclosed in U.S. Pat. No. 4,892,532, which is incorporated herein by this reference.

The central absorbent layer 24 can be comprised of any absorbent material such as for example, cellulose, thermoplastic copolymers, cotton, or any of a number of the commonly available absorbent materials, including these materials containing or being impregnated with a gelling agent. The preferred central absorbent layer 24 comprises cotton fibers and a gelling agent to cause any liquid entering the central absorbent layer 24 to gell upon contact with the gelling agent. The use of such a gelling agent helps prevent fluid leakage to the wearer's garments and to reduce moisture contact with the wearer's skin. Generally, the central absorbent layer 24 is composed of such a material or blend of materials that the central absorbent layer 24 will be as thin as possible and will not expand or will only expand a small amount upon the addition of fluid thus reducing, for example, the stretching of and the possibility of showing through the wearer's garments.

The central absorbent layer 24 has a cross-section of graduated thickness. As shown more clearly in FIGS. 3 and 4, central absorbent layer 24 is thinnest around the periphery of the pads 10 and gradually thickens to its thickest point at the thickened nipple area 26 which is located generally in the center of the pads. As most fluid will be present around the nipple area of the pads 10 due to leakage from the nipple, and along the bottom edge of the pads 10 due to gravitation, the top and side edges of the periphery of the pads 10 may contain a thinner layer of central absorbent layer 24. As the area of the pads 10 immediately adjacent the nipple is subjected to the greatest amount of fluid, a greater amount of central absorbent layer 24 is provided immediately adjacent to the nipple. Due to the possible downward flow of the fluid by gravitation, the lower peripheral edge of the pad has a somewhat thicker layer of central absorbent layer 24 then the top or sides of the periphery of the pads. However, the layer of central absorbent layer 24 along the lower edge of the pads need not be as thick as at the thickened nipple area 26.

The central absorbent layer 24 preferably comprises an ultrahigh fluid absorbing composition so as to absorb the most fluid with the least expansion. Without limitation, examples of suitable central absorbent layers 24 include hydrophilic microfibers such as the hydrophilic nylon copolymer microfibers disclosed in U.S. Pat. No. 4,923,454, which is incorporated herein by this reference. Preferably, the central absorbent layer 24 further will comprise a gelling agent which will cause the liquid entering the central absorbent layer 24 to become gelled to further help prevent leakage from the pads 10. A suitable gelling agent is a hydrogel-forming polymeric gelling agent such as hydrolyzed acroylonitrile grafted starch, polyacrylate grafted starch, polyacrylates, maleic anhydride-based copolymers, other substantially water-insoluble, slightly cross-linked, partially neutralized polymers, and combinations thereof, such as disclosed in U.S. Pat. No. 4,935,022, which is incorporated herein by this reference. Of course, it is obvious that any suitable liquid absorbent material or gelling agent is appropriate for use as the central absorbent layer 24.

The outer moisture resistant layer 18 is a generally liquid impervious backing sheet which forms a barrier between the central absorbent layer 24 and the wearer's garments and prevents the fluid and/or gel contained within the central absorbent layer 24 from passing through to the outside of the breast pads and contacting or seeping into or through the wearer's garments. The outer moisture resistant layer 18 preferably is made from a light plastic or rubber latex or other polymer which will not make a rustling or crinkling noise when flexed or deformed. Additionally, the outer moisture resistant layer 18 preferably is made from a material which will expand or stretch if the breast expands when producing milk and will contract if the breast contracts during and after nursing. The outer moisture resistant layer 18 can be colored so as to match the natural skin tone of the wearer.

Referring now to FIGS. 2 and 4, it can be seen that the outer moisture resistant layer 18 covers the entire outer surface of the pads 10. Along approximately the bottom one-half of each pad 10, that is from approximately the point 16 to approximately midway around the lower, rounded portion of the tear drop, the moisture-resistant layer wraps around the edge of the pad and upwardly a short distance along the interior of the pad so as to form a lip or dam 20 of outer water resistant layer 18 along the lower interior edge portion of the pad 10. This formation creates a fluid well 28 having an outer edge comprising moisture-resistant layer 18 and filled with central absorbent layer 24. That is, a quantity of central absorbent layer 24 is located between outer moisture resistant layer 18 and lip or dam 20. As central absorbent layer 24 becomes filled with fluid, gravity may cause the fluid to flow to the bottom edge of the central absorbent layer 24. This fluid is prevented from seeping out of the bottom edge of the pads 10 by the wrap around structure of outer moisture resistant layer 18.

The three layers may be bonded together in any conventional manner. A preferred method is to bond outer moisture resistant layer 18 to inner wicking layer 22 along their peripheral edges. As the bond between the outer moisture-resistant layer 18 and the inner wicking layer 22 at the lower edge portion of the pads 10 is located somewhat away from the actual peripheral edges of the pads, moisture contained within the central absorbent layer 24 is prevented from leaking around the bond. The bonded structure forms an envelope in which the central absorbent layer 24 is contained. Although it is not necessary to bond the central absorbent layer 24 to either the inner wicking layer 22 or the outer moisture-resistant layer 18, this can be done to prevent extraneous movement of the central absorbent layer 24 within the structural envelope and to assist in a better wicking of fluid from the inner wicking layer 22 to the central absorbent layer 24.

The pads 10 are generally dome-like in structure so as to provide a better fit within the generally dome-like structure of the typical brassiere cup 34 and to provide a more comfortable fit around the generally dome-like natural shape of the typical female breast. As the materials comprising the inner wicking layer 22 and the outer moisture resistant layer 18 generally are flexible and less likely to retain a manufactured dome-like shape, the central absorbent layer 24 can be manufactured to provide the desired dome-like shape described above. The outer moisture resistant layer 18 of the pads 10 are contoured either by shaping during the manufacturing process or by the shape of the central absorbent layer 24 so as to fit within and compliment a typical brassiere cup 34. By having such a contoured outside shape, the pads 10 will correspond well with the interior shape of a brassiere cup 34, help prevent extraneous movement of the pads 10 within the brassiere 10, and decrease visibility of the pads through the wearer's garment. The inner wicking layer 22 of the pads 10 also are contoured either by shaping during the manufacturing process or by the shape of the central absorbent layer 24 so as to conform to the natural shape of the female breast. By having such a contoured inside shape, the pads 10 also will correspond well with the exterior shape of the female breast and provide increased comfort to the wearer and help prevent extraneous movement of the pads 20 around the breast.

The pads are provided in pairs including a right pad 12 and a left pad 14 for use in the right cup and left cup, respectively, of a brassiere 32. The pads 10 are generally dome-like in appearance and are contoured to approximate the nature contours of the female breasts. The natural differences in shape between the right breast and the left breast necessitate the need for a right pad 12 and a left pad 14.

The pads 10 are of such a size that they both will fit and encompass the entire breast and will be sized so as to contact the majority of the inner surface of the brassiere cup 34. The sizing of the pads 10 has several functions. By encompassing the entire breast, the pads 10 are much more comfortable to wear. By contacting the entire inner surface of the brassiere cup 34, the pads 10 are much less likely to move within the brassiere. Additionally, by being the same approximate size as the brassiere cups 34, the pads 10 are less likely to show through the brassiere 32 and the wearer's garments. Generally, the pads 10 will be supplied in three different sizes, small, medium, and large, to accommodate the various sized women. The general interior shape of the brassiere cup 34 for typical small, medium and large brassiere sizes is taken into account when creating the outer contoured shape of the pads 10.

Referring now to FIG. 5, the pads 10 can be seen as in actual use. The wearer 30 is wearing a typical brassiere 32, which may be a maternity or nursing brassiere, comprising brassiere straps 36 and brassiere cups 34. The right pad 12 is shown in its proper position inserted within the brassiere cup 34 between the brassiere 32 material and the breast. As can be seen, the right pad 12 encompasses the entire breast and generally fills the entire brassiere cup 34. The left pad 14 is shown in cross-section within a brassiere cup 34. The upper tear drop point 16 on both the right pad 12 and the left pad 14 is shown in its proper position at the bra strap 36 and brassiere cup 34 juncture. The thickened nipple area 26 of the left pad 14 is a shown immediately adjacent to the nipple of the wearer 30. The lip or dam 20 created from the outer moisture resistant layer wrapping around the bottom edge of the left pad 14 creates the well 28. The lip or dam 20 may extend a short distance upwardly along the interior of the pads 10 so it just contacts the wearer 30, or may wrap around a sufficient distance such that a greater portion of the lip or dam 20 contacts the breast of the wearer. The lip or dam 20 should not extend upward so far so as to contact the wearer's nipple. As the pads 10 become loaded with fluid, they are removed from the brassiere 32 and disposed. New pads 10 then are substituted for as long as they are needed.

From the above description and the accompanying figures, it can be seen that the breast pads for nursing mothers disclosed and described in this specification achieve the objects and advantages attributed to this invention above. While this description and the accompanying figures show the best mode of the invention as contemplated by the inventors at this time, they are meant for illustrative purposes and not to limit the invention as defined in the appended claims.

What is claimed is:

1. A contoured breast pad for use by a human female wearer who has at least one breast, said pad being placed between a brassiere cup worn by the wearer and said breast, the brassiere cup having at least an inner surface configured to accommodate a human female breast, said pad having an interior concave surface and an exterior concave surface and comprising an inner fluid wicking layer, an outer fluid resistant layer, a central fluid absorbent layer located between said inner layer and said outer layer and a peripheral edge;

said inner layer having a soft and comfortable texture configured to be against said breast and embodying a wicking quality which wicks fluid contacting said inner layer through said inner layer into said central fluid absorbent layer such that said inner layer remains relatively dry;

said outer layer comprising a moisture resistant material;

said central layer comprising a fluid absorbent material which will absorb and retain fluid upon contact; and said peripheral edge comprising an upper point, an inner side edge, an outer side edge, and a rounded bottom edge;

wherein a portion of said outer layer wraps around said rounded bottom edge and extends upwardly along the interior concave surface of said pad, said inner layer and said outer layer are bonded together creating a hollow interior space in which said central fluid absorbent layer is enveloped, and said breast pad has a tear drop shape and hemispherical cross-section and is of such a size and shape that it will conform to and encompass said breast and will conform to and contact the inner surface of the brassiere cup.

2. The breast pad as claimed in claim 1, wherein a portion of said outer layer wraps around the outer side edge and extends inwardly along the interior concave surface of said pad.

3. The breast pas as claimed in claim 2, further comprising a plurality of sizes specifically sized to fit a plurality of different size breasts.

4. The breast pad as claimed in claim 2, wherein said portion of said outer layer which wraps around the outer side edge of said pad forms an inner wall which together with said outer layer forms a fluid well, said fluid well being filled with said central absorbent layer.

5. The breast pad as claimed in claim 4, wherein said breast is a left breast, said breast pad specifically contoured for the left breast.

6. The breast pad as claimed in claim 4, wherein said breast is a right breast, said breast pad specifically contoured for the right breast.

7. The breast pad as claimed in claim 4, wherein said inner layer is a cotton mesh.

8. The breast pad as claimed in claim 4, wherein said central fluid absorbent layer comprises a fiber selected from the group consisting of cotton fibers, cellulose fibers, thermoplastic fibers, rayon fibers, polyester fibers, macerated wood pulp or fluff.

9. The breast pad as claimed in claim 8, wherein said central fluid absorbent layer further comprises a gelling agent.

10. The breast pad as claimed in claim 4, wherein said breast comprises a nipple, wherein said central fluid absorbent layer has a graduated thickness wherein said central fluid absorbent layer is thinnest around said peripheral edge and is thickest where said pad is immediately adjacent to said nipple.

11. The breast pad as claimed in claim 10, wherein the thickness of said central absorbent layer around said peripheral edge also is graduated, said central absorbent layer being thinnest proximate to said upper point and being thicker proximate to said rounded bottom edge, and said thickness of said central absorbent layer around said peripheral edge being thinner than the thickness of said central absorbent layer where said pad is immediately adjacent to said nipple.

12. The breast pad as claimed in claim 1, wherein said portion of said outer layer which wraps around the rounded bottom edge of said pad forms an inner wall which together with said outer layer forms a fluid well, said fluid well being filled with said central absorbent layer.

13. The breast pad as claimed in claim 1, wherein said outer layer further comprises a material which has an elastic quality allowing said outer layer to expand and contract.

14. The breast pad as claimed in claim 1, wherein said hemispherical cross-section, taken from said rounded bottom edge to said upper point, comprises a slope which gradually flattens out form said rounded bottom edge to said upper point.

15. A contoured breast pad for placement within a brassiere cup and for contacting a human female breast accommodated therein, said breast pad having an interior surface, an exterior surface and a periphery and comprising an inner fluid wicking layer, an outer moisture resistant layer, and a central absorbent layer, each of which has a peripheral edge and a center, wherein said central layer has a graduated thickness being thinnest around its peripheral edge and thickest in its center;

said outer layer comprises said exterior surface and wraps around at least a portion of said periphery of said pad and extends inwardly a certain distance along said interior surface; and said pad is of such a size that said exterior surface fits within said brassiere cup and said interior surface will conform to said human female breast.

* * * * *